(12) United States Patent
Krieger et al.

(10) Patent No.: US 11,452,626 B2
(45) Date of Patent: Sep. 27, 2022

(54) VARIABLE RADIAL STIFFNESS AND VARIABLE DIAMETER INTRALUMINAL DEVICE

(71) Applicant: COOK MEDICAL TECHNOLOGIES LLC, Bloomington, IN (US)

(72) Inventors: Joshua F. Krieger, Bloomington, IN (US); Richard A. Swift, South Bend, IN (US); Seoggwan Kim, West Lafayette, IN (US); Susan G. Sahlgren, Copenhagen (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 190 days.

(21) Appl. No.: 16/559,953

(22) Filed: Sep. 4, 2019

(65) Prior Publication Data

US 2019/0388254 A1 Dec. 26, 2019

Related U.S. Application Data

(62) Division of application No. 15/256,873, filed on Sep. 6, 2016, now Pat. No. 10,441,447.

(60) Provisional application No. 62/217,345, filed on Sep. 11, 2015.

(51) Int. Cl.
*A61F 2/915* (2013.01)
*A61F 2/844* (2013.01)

(52) U.S. Cl.
CPC .............. *A61F 2/915* (2013.01); *A61F 2/844* (2013.01); *A61F 2002/91558* (2013.01); *A61F 2002/91583* (2013.01); *A61F 2250/0018* (2013.01); *A61F 2250/0039* (2013.01); *A61F 2250/0042* (2013.01)

(58) Field of Classification Search
USPC ..................................... 623/1.1–2.15, 23.68
See application file for complete search history.

(56) References Cited

U.S. PATENT DOCUMENTS

| | | | |
|---|---|---|---|
| 5,817,102 A | 10/1998 | Johnson et al. |
| 5,827,321 A | 10/1998 | Roubin et al. |
| 7,001,425 B2 | 2/2006 | McCullagh et al. |
| 7,258,697 B1 | 8/2007 | Cox et al. |
| 8,778,008 B2 | 7/2014 | Amplatz et al. |
| 2004/0243216 A1 | 12/2004 | Gregorich |
| 2009/0125095 A1 | 5/2009 | Bui et al. |
| 2010/0023132 A1 | 1/2010 | Imran |
| 2010/0299911 A1 | 12/2010 | Gianotti et al. |
| 2011/0106237 A1 | 5/2011 | Bonsignore et al. |
| 2012/0253454 A1 | 10/2012 | Costello |
| 2013/0110253 A1 | 5/2013 | Gill et al. |

(Continued)

*Primary Examiner* — Yashita Sharma
(74) *Attorney, Agent, or Firm* — Crowell & Moring LLP

(57) ABSTRACT

The present disclosure describes intraluminal support devices having high radial stiffness regions with smaller diameter and low radial stiffness regions with larger diameter. When deployed to the vasculature of a patient in need of treatment, the high radial stiffness region is sized such that it has approximately the diameter of the vessel in need of treatment, so that it produces substantially zero chronic radial force when the vessel is not being subjected to external compression. The low radial stiffness regions anchor the device to the vessel wall and provide a less-abrupt transition from the high radial stiffness structure. Methods of making and using such devices are also described.

16 Claims, 4 Drawing Sheets

(56) References Cited

U.S. PATENT DOCUMENTS

2013/0204311 A1    8/2013   Kunis
2014/0074220 A1    3/2014   Clerc et al.
2015/0081000 A1    3/2015   Hossainy et al.

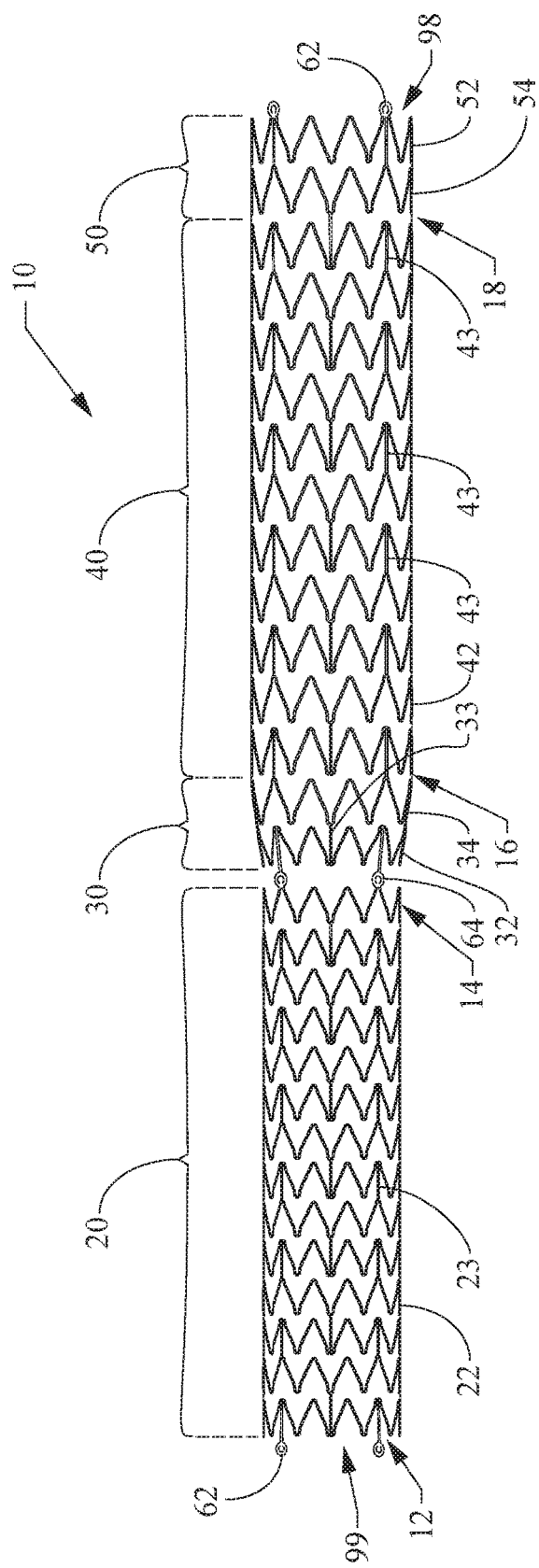
FIG. 2
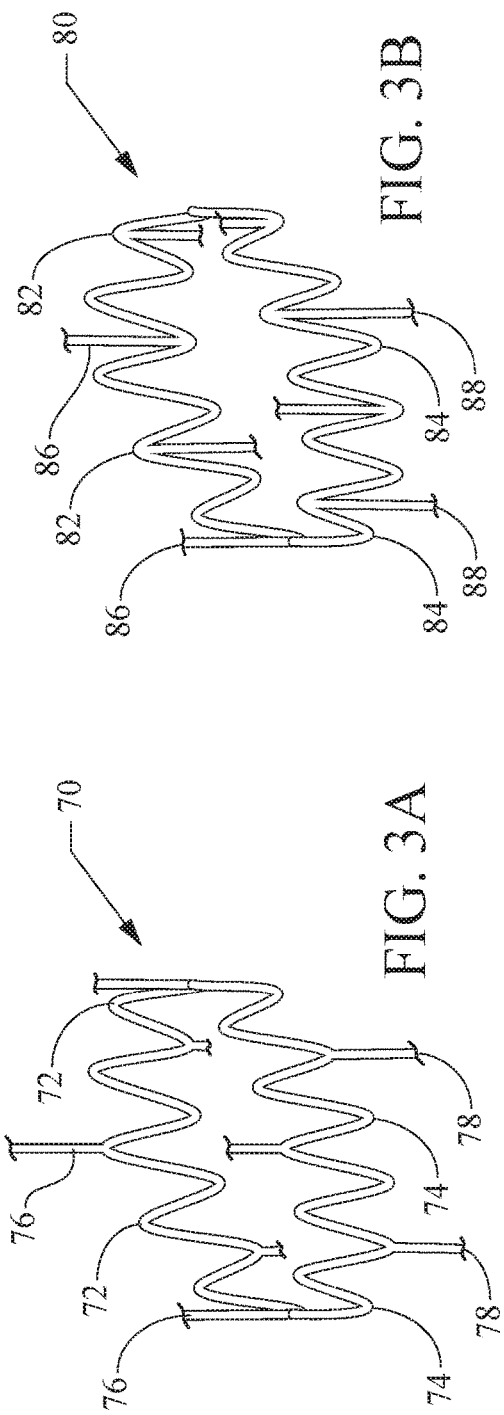
FIG. 3A
FIG. 3B

VARIABLE RADIAL STIFFNESS AND VARIABLE DIAMETER INTRALUMINAL DEVICE

CROSS-REFERENCE TO RELATED APPLICATIONS

This application is a divisional application from U.S. Non-Provisional application Ser. No. 15/256,873, filed on Sep. 6, 2016, which claims the benefit of priority under 35 U.S.C. § 119(a) to U.S. Provisional Application No. 62/217,345, filed Sep. 11, 2015 all of which are hereby incorporated by reference in their entirety.

BACKGROUND

The present disclosure relates to medical devices. More particularly, the invention relates to an intraluminal support device having a region which produces a high radial force (HRF) and a region which produces a low radial force (LRF) for treating a vascular malady such as a compressive lesion.

Intraluminal support devices, such as stents, are used to maintain the patency of blood vessels. As part of the common practice of using self-expanding intraluminal support devices, the device is deployed with a set size mismatch. The device has a larger diameter than the natural diameter of the target vessel. Such a mismatch functions to prevent migration of the device through the vasculature and to supply a radial force against the vessel wall.

An excessive amount of radial force, however, can have a negative effect and lead to increased late lumen loss. As stretch receptors are triggered by chronic radial force, the vessel wall thickens inward to equalize the force supplied by the implant. In some aspects, such thickening may be intimal hyperplasia. Such vessel wall thickening can also be seen in conditions of venous hypertension, as pressure increases activate the same physiological mechanisms. As such, the use of large high radial force for treating compressive lesions, such as May-Thurner Syndrome or compressive tumors, is a challenge, as high enough radial force to maintain vessel patency must be balanced against low enough levels of radial force to prevent or slow remodeling. Moreover, vessels with stenosis may require treatment with such an intraluminal support device in order to increase outflow from the deep venous system as part of a treatment regimen for chronic venous insufficiency (CVI).

There is a need for improved intraluminal support devices which produce high enough radial force to remain in place in the vasculature and maintain vessel patency without triggering vessel remodeling due to the production of a chronic high radial force.

BRIEF SUMMARY

In one aspect, a radially expandable intraluminal support device for implantation into a lumen of a body vessel having a nominal diameter is provided. The device includes a first tubular portion having a first end extending to a second end, defining a longitudinal axis therethrough. The first tubular portion includes at least one ring structure and has a first diameter along a first length of the first tubular portion in an expanded state. In a fully expanded state, the first diameter is greater than the nominal diameter, and the first tubular portion has a first radial stiffness. The intraluminal support device has a second tubular portion having a third end extending to a fourth end about the longitudinal axis. The second tubular portion includes at least one ring structure and a second diameter along a second length of the second tubular portion in the expanded state, the second diameter being less than the first diameter. In the fully expanded state, the second diameter is substantially equal to the nominal diameter. The second tubular portion has a second radial stiffness greater than the first radial stiffness. The device includes a transition portion disposed between the first tubular portion and the second tubular portion. The transition portion is connected to the second end and the third end and includes at least one ring structure. The transition portion has a profile tapering between the first diameter and the second diameter such that, at any point along its length, the transition portion has a diameter between the first diameter and the second diameter, inclusive, and the radial stiffness of the transition portion increases progressively along its length, the radial stiffness of the transition portion increasing from the first radial stiffness at a position at or near the second end to the second radial stiffness at a position at or near the third end. The device may be of unitary construction.

In another aspect, a radially expandable intraluminal support device for implantation into a lumen of a body vessel having a nominal diameter is provided. The device includes a first tubular portion having a first end extending to a second end defining a longitudinal axis therethrough. The first tubular portion comprises a plurality of first rings disposed coaxial with each other, each first ring individually including a plurality of first segments arranged as a plurality of peaks and valleys, each first segment having a first length. Each ring has its respective peaks aligned with the peaks of all other rings to define an in-phase relationship of the rings along the first tubular portion. The first tubular portion is substantially cylindrical in shape in an expanded state and has a first diameter. The first tubular portion has a first radial stiffness. The device includes a second tubular portion having a third end and extending to a fourth end about the longitudinal axis. The second tubular portion includes a plurality of second rings disposed coaxial with each other. Each second ring individually comprises a plurality of second segments arranged as a plurality of peaks and valleys. Each second segment of a second ring has a second length less than the first length, each second ring having its respective peaks aligned with the peaks of all other second rings to define an in-phase relationship of the second rings along the second tubular portion. The second tubular portion is substantially cylindrical in shape in the expanded state and has a second diameter which is smaller than the first diameter. The second tubular portion has a second radial stiffness greater than the first radial stiffness. The device also includes a third tubular portion having a fifth end and extending to a sixth end about the longitudinal axis. The third tubular portion includes a plurality of rings disposed as in the first tubular portion and the third tubular portion has a diameter greater than the second diameter. The third tubular portion has a third radial stiffness which is less than the second radial stiffness. The device includes a first transition portion including at least one ring between the first tubular portion and the second tubular portion. The first transition portion is connected to the second end and the third end. The device includes a second transition portion comprising at least one ring between the second tubular portion and the third tubular portion, the first transition portion being connected to the fourth end and the fifth end. The first transition portion has a profile tapering such that its diameter, at any point along its length, is between the first diameter and the second diameter, inclusive. The first transition portion has a radial stiffness which increases progressively along its length, the radial stiffness of the second transition portion increasing from the first radial stiffness at a position at or near the second end to the second radial stiffness at a position at or near the third end. The second transition portion has a profile tapering such that its diameter, at any point along its length, is between the third diameter and the second diameter, inclusive. The second transition portion has, at any point along its length, a radial stiffness which increases progressively along its length, the radial stiffness of the second transition portion increasing from the third radial stiffness at a position at or near the fifth end to the second radial stiffness at a position at or near the fourth end. The intraluminal support device is of monolithic construction. The second tubular portion may be disposed at the location of the lesion, and the first tubular portion may be disposed away from the lesion for anchoring the device within the body vessel and/or holding the vessel open.

Further objects, features, and advantages of the present invention will become apparent from consideration of the following description and the appended claims when taken in connection with the accompanying drawings.

BRIEF DESCRIPTION OF THE DRAWINGS

The drawings are purely schematic illustrations of various aspects of the invention and are not necessarily to scale, unless expressly stated.

The terms "substantially" or "about" used herein includes variations in the recited characteristic or quantity that are functionally equivalent to the quantity recited, such as an amount that is equivalent to the quantity recited for an intended purpose or function. In the case of a numerical quantity, the terms "substantially" or "about" shall mean a range consisting of a value 20% less than the recited value to a value 20% greater than the recited value, inclusive.

FIG. 2 is a side view of a first embodiment of a device in accordance with the principles of the present disclosure;

FIGS. 3A and 3B are close-up views of ring structures as used in one embodiment of a device of the present disclosure;

DETAILED DESCRIPTION OF THE DRAWINGS

While the present invention has been described in terms of certain preferred embodiments, it will be understood that the invention is not limited to the disclosed embodiments, as those having skill in the art may make various modifications without departing from the scope of the following claims.

As used herein, the term "nominal diameter" is taken to mean the expected or predicted average diameter of a body vessel in which a device is to be implanted. Nominal diameter of many body vessels will fall within the range from 4 mm to about 30 mm in diameter, inclusive.

Figure 1A:
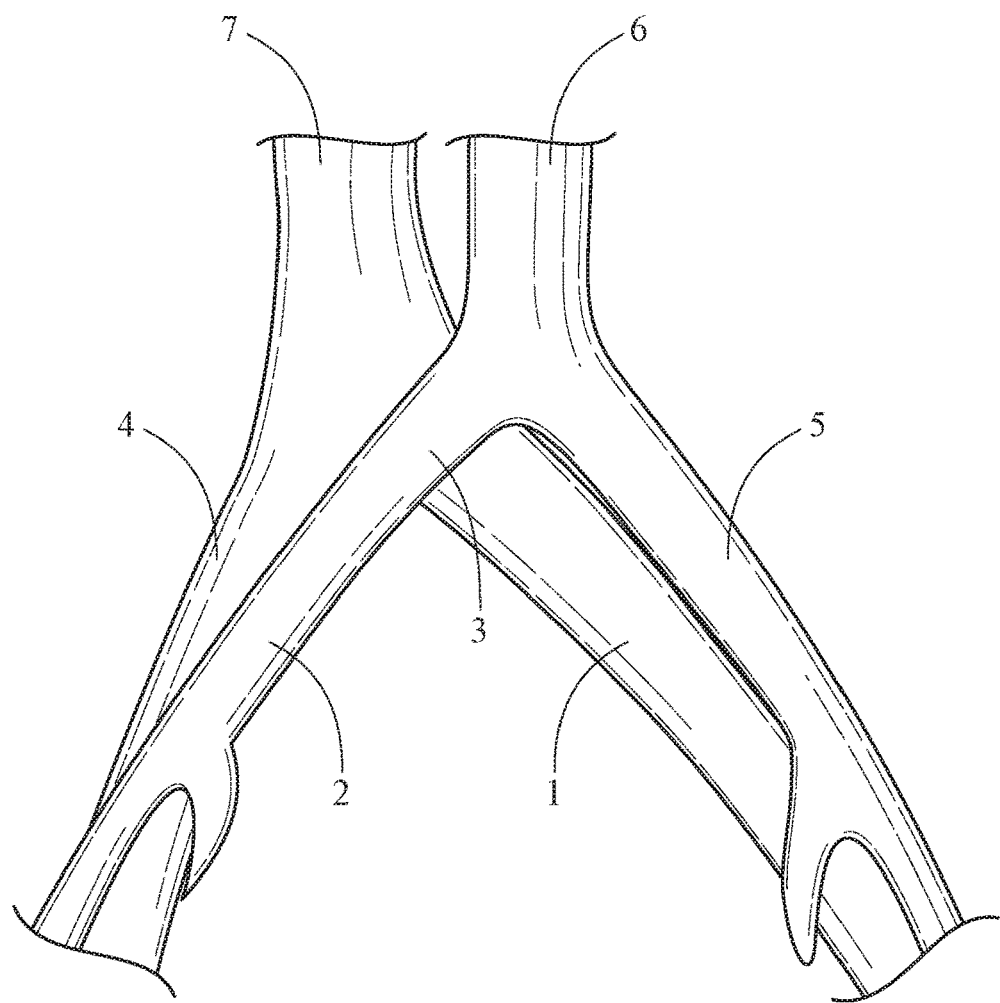
FIGS. 1A and 1B are schematic representations of the major blood vessels of the pelvic region of a human.

FIG. 1A is a view of the arteriovenous anatomy of the pelvic region of a human. The major body vessels are illustrated. The left common iliac vein 1 and right common iliac vein 4 branch off from the inferior vena cava 7 at about the level of the fifth lumbar vertebra and act to drain blood from the pelvis and lower limbs. Lying anterior to the common iliac veins are the left common iliac artery 5 and right common iliac artery 2, which branch from the aorta 6. Significantly, the right common iliac artery 2 overlies a portion of left common iliac vein 1 at compression point 3.

Figure 1B:
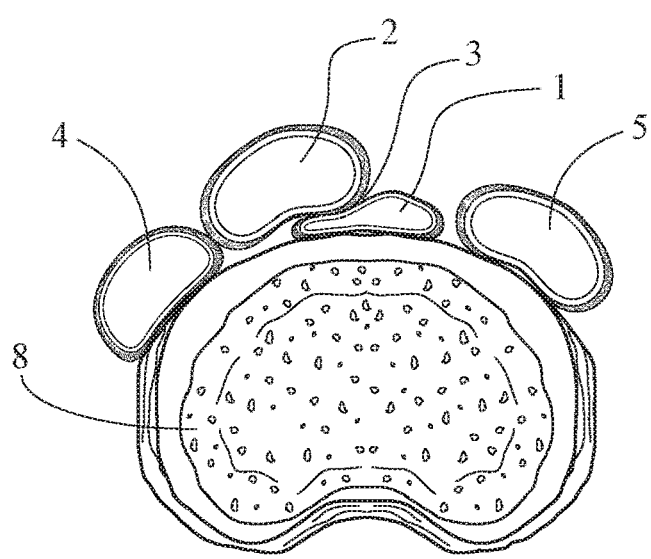

FIG. 1B is a cross-sectional view of the anatomy shown in FIG. 1A as would be seen in a patient suffering from a compressive lesion, such as May-Thurner Syndrome. As seen in this view, the left common iliac vein 1 has been compressed at focus 3 on vertebra 8 by right common iliac artery 2, greatly decreasing the effective diameter of the vein and severely inhibiting blood flow therethrough. Physiological consequences of such a compression can include discomfort, swelling, pain, and blood clots including deep vein thrombosis (DVT). Such a compression could also be created at this point or at another point in the vascular system by a growth, for example of a tumor, which presses down on a vein from the outside.

To relieve these symptoms and recover vascular patency, an implant including a stent may be used. However, the pressure on the vessel wall and chronic outward force produced by such a device may have problematic side effects since the device employed must overcome the force of compression.

Overcompensation with excess force can lead to physiological remodeling of the vessel, causing cell growth inside the treated vein to occur. This thickens the inner lining of the vessel and once again reduces the effective diameter for blood flow therethrough.

FIG. 2 is a first embodiment of a device 10 which can assist in treating a compressive lesion in a blood vessel. The device includes a first tubular portion 40 which extends from first end 18 to second end 16, a second tubular portion 20 which extends from third end 14 to fourth end 12, and a transition zone 30 between the first tubular portion 40 and the second tubular portion 20.

The first tubular portion 40 and the second tubular portion 20 are both substantially cylindrical in order to best fit the profile of a vessel into which they might be implanted. Veins in particular have very little actual structure; fluid flow therethrough creates the typical tubular shape. The diameter of the first tubular portion 40 is slightly larger than the diameter of second tubular portion 20, and the transition zone 30 is constructed in such a way as to avoid an abrupt transition between the stiffness of one body and that of the next.

In the illustrated embodiment, the first tubular portion 40 and the second tubular portion 20 are made of a series of ring structures which are in turn made up of a number of struts or segments. These segments are positioned end-to-end to form an undulating pattern which gives each ring a peak-and-valley type arrangement. However, many other designs are possible for creating these substantially tubular or cylindrical device bodies.

FIGS. 3A and 3B are close-up views of ring structures associated with the design of the device illustrated in FIG. 2. In order to construct a tubular device with multi-ring construction, two different interconnection schemes are employed. The ring of FIG. 3A illustrates a ring 70 having 24 segments connected to form twelve peaks 72 and twelve valleys 74. Extending upward from every third peak 72 is a connector segment (or T-bar) 76, and at each third valley 74 is a downward-extending T-bar 78 substantially halfway, as measured circumferentially, between the T-bars 76.

As used herein, the term "connected" means contacting, touching, or neighboring. Portions of a device which are "connected" may be connected directly or indirectly to one another. Different regions of a device of unitary construction are considered to be connected together via the device itself, and the condition of being connected does not presume that the device was made of separate components that needed to be connected together, such as by an adhesive or a weld, to achieve such connection. However, the term "connected" is not exclusive to describing different portions of a unitary device, but may also refer to two separately-formed pieces which are connected by, for example, a welding step.

Ring 80 of FIG. 3B, on the other hand, illustrates a ring that would be suitable for being positioned longitudinally adjacent the ring of FIG. 3A, as the upward T-bars 86 extend from valleys 84, and the downward T-bars 88 extend from peaks 82. The terms upward and downward are used to describe the directionality of the T-bars as illustrated in FIGS. 3A and 3B and should not be interpreted as limiting the positioning of structures of the device. If the rings of FIGS. 3A and 3B were to be joined as in FIG. 2, T-bar 76 and T-bar 88 would represent the same connector segment of the device as one another, and T-bar 78 and T-bar 86 would represent the same connector segment of the device as one another. In the device, the connectors or T-bars lie substantially parallel to a longitudinal axis which runs through the center of the device.

The plurality of rings of a body are disposed coaxial with each other, with each ring individually comprises a plurality of first segments arranged as peaks and valleys. Each ring may be positioned with its peaks aligned with the respective peaks of all other rings of the device to define an in-phase relationship of the rings along the body. Such a spatial arrangement may be advantageous for collapsing the device so that it can be placed in a delivery system with optimal packing efficiency.

The geometry of the rings and connecting segments (or T-bars) give the device its physical characteristics in part. Measuring longitudinally from a peak to a valley of a ring structure gives a quantity referred to herein as cell length. With segments or struts of equal width (circumferentially) and thickness (in the radial dimension), a ring made to have a shorter cell length will produce a greater radial force than one with a larger cell length.

Other aspects of the struts can be modified to impact radial stiffness. It is to be understood that radial stiffness is the property of a tubular device which dictates the production of radial force when that device is implanted in a body vessel. Radial stiffness is determined by the ability of a cylindrical member to resist a compressive force applied perpendicular to the surface of the cylinder, in some instances all the way around the cylinder circumferentially and uniformly. Measurement of such uniform cylindrical compression can be measured by using a standard radial force compression machine, which provides an aperture which closes uniformly around the cylinder and reports force generated (that is, compression resisted.) The force applied, in being perpendicular to the surface of the tubular member, is also applied in planes perpendicular to a longitudinal axis running through the tubular member.

To alter the radial stiffness, and therefore the radial force, produced by the device, the following modifications may be made. Thickening the struts in the radial dimension will serve to increase radial force in a linear fashion. Making struts wider in the circumferential direction increases radial force in a cubic relation. Thus, to maximize radial force generated by a particular segment minimizing cell length while maximizing cell width will produce the desired result.

Alternative tests of compressibility, radial force generation, and radial stiffness include flat plate compression, in which the tubular object is placed between two parallel plates and subjected to crushing force.

The T-bars or connecting members provide connectivity between ring structures and modulate flexibility. In general, a longer T-bar will result in a more flexible device.

Returning to FIG. 2, the rings 42 of first tubular portion 40 have a greater cell length than the rings 22 of the second tubular portion 20. In the illustrated embodiment, width and thickness are constant across the entire length of the device, and as a result second tubular portion 20 produces a greater radial force than does first tubular portion 40. Transition zone 30 comprises two rings 32 (attached to third end 14) and 34 (attached to second end 16), with ring 32 having a greater cell length than the rings which make up the second tubular portion 20, ring 34 having a greater cell length than ring 32, and the rings which make up the first tubular portion 40 having a greater cell length than ring 34. Hence, the transition zone 30 provides a gradient of radial force to move between the high radial force provided by second tubular portion 20 and the low radial force provided by first tubular portion 40. The profile of transition zone 30 tapers such that its diameter, at any point between that of the first tubular portion 40 and the second tubular portion 20, has a value which is equal to or between the diameter of first tubular portion 40 and second tubular portion 20.

It may also be said of a transition zone (or transition portion) that the transition portion has a radial stiffness. As used in this disclosure, the concept of radial stiffness of a tapering transition zone is meant to be viewed with an eye toward the two bodies the transition zone provides a transition between. In such a case, the radial stiffness of the transition zone, at any point along its length, will be equal to the radial stiffness of the two bodies it bridges, or intermediate of these two values.

A transition portion or transition zone may create a substantially linear transition in radial stiffness, diameter, or both. That is, the diameter may increase substantially linearly from the smaller diameter tubular portion of the device to the larger diameter tubular portion of the device. Such an increase may be steady, and may be progressive. Other transitions are possible, such as a curvilinear transition, an undulating transition, or any other style of transition. A linear transition in particular can be considered to taper.

A transition portion can have a radial stiffness which increases progressively along its length. The radial stiffness of the transition portion increases within a range which encompasses, or is increased from, the radial stiffness of the tubular portion which has the relatively lower radial stiffness. This increase begins at a position which is at, or near (that is, within one ring structure of) the end of that tubular portion to which the transition portion is connected. The radial stiffness then increases along the length toward the end of the higher radial stiffness body. The increase continues until the transition portion has a radial stiffness which is equal to or is slightly less than the radial stiffness of the higher radial stiffness body at a position at, or near (that is, within one ring structure of) the end of the higher radial stiffness body to which the transition portion is connected.

In the embodiment illustrated in FIG. 2, end cell pair 50 is attached to first end 18. The end cell pair 50 is made up of ring 54, attached at first end 18, and ring 52, which is the terminal ring of the device at device end 98. As in the transition portion, ring 54 has a greater cell length than the rings of first tubular portion 40, and ring 52 has a greater cell length than that of ring 54, thus decreasing radial force at the far end of the device in order to minimize force applied to the vessel wall at its extreme end and transition to a portion of a vessel which is effectively only held open by pulsatile flow of blood therethrough under normal circumstances.

Optionally, second tubular portion 20 may be equipped with a similar set of end cells.

In some cases, end cell pairs will not be necessary since the radial stiffness of the end of the device may be sufficiently low so as to not require further decrease to avoid an abrupt transition in properties from the portion of the vessel which has an implant to one which does not.

In the embodiment of FIG. 2, the diameter of the second tubular portion 40 is smaller than the diameter of the first tubular portion 20. As mentioned above, a patient benefiting from treatment with a device of this construction may benefit from a relatively smaller chronic radial force against the point of the vessel where compression is occurring, but will benefit from the vein being held patent and being supported by a crush-resistant device. Thus the device should create a high radial force when necessary (i.e., when an external compressive force is acting upon the vein into which it has been implanted), but under ordinary circumstances the magnitude of the chronic radial force supplied by the device should be minimized. This is in contrast to what is generally practiced in stenting applications, in which stents producing high chronic radial force are deliberately selected for treatment of body lumens due to their tendency to remain where deployed and their ability to keep said lumens patent.

The smaller diameter is fit to approximately the diameter of the portion of the vessel to be treated, such that the device, when implanted, does not produce an excessive radial force unless the vessel is compressed, and merely makes slight to no contact with the internal wall of the vessel under non-compressive conditions. In contrast, the larger diameter regions of the device, such as first tubular portion 20, are sized to exert a force against the vessel in order to anchor it within the vessel and prevent the device from moving in the vessel after implantation.

In one embodiment, a self-expanding intraluminal support device in accordance with the principles of the present disclosure can be made of a shape memory material. One example of a shape memory material is a shape memory metal, in particular a class of nickel-titanium alloys, including those marketed under the name NITINOL. Such alloys are known for their shape memory and pseudoelastic properties. As a shape memory material, such a nickel-titanium alloy is able to undergo a reversible thermoelastic transformation between certain metallurgical phases.

In another embodiment, the device may be balloon-expandable rather than self-expanding.

Generally, the thermoelastic shape memory effect allows the alloy to be shaped into a first configuration while in the relative high-temperature austenite phase, cooled below a transition temperature or temperature range at which the austenite transforms to the relative low-temperature martensite phase, deformed while in a martensitic state into a second configuration, and heated back to austenite such that the alloy transforms from the second configuration to the first configuration. The thermoelastic effect is often expressed in terms of the following "transition temperatures": $M_s$, the temperature at which austenite begins to transform to martensite upon cooling; $M_F$, the temperature at which the transformation from austenite to martensite is complete; $A_s$, the temperature at which martensite begins to transform to austenite upon heating; and $A_f$, the temperature at which the transformation from martensite to austenite is complete.

As a pseudoelastic material, nitinol is able to undergo an isothermal, reversible transformation from austenite to martensite upon the application of stress. This stress-induced transformation to martensite typically occurs at a constant temperature between $A_s$ and $M_d$, the maximum temperature at which martensite can exist in an alloy even under stress conditions. The elasticity associated with the transformation to martensite and the resulting stress-induced martensite make pseudoelastic nitinol suitable for applications requiring recoverable, isothermal deformation.

A device made from a nickel-titanium shape memory material can be heat set to retain its shape after implantation. In one embodiment, the device may have a remembered state of well below body temperature such that at body temperature it returns to its original shape. In one example, the temperature may be about ten to about fifteen degrees Celsius.

FIG. 2 represents a device which has a zone of high-radial force (HRF), a transition zone (TZ), a low radial force zone (LRF), and an end cell pair. The HRF zone provides crush resistance. This zone is sized to substantially the nominal diameter of the vessel to be treated and only exerts a force when the vessel is subjected to an external pressure. An increase in material thickness would also assist with crush resistance.

The sizing of a HRF zone (or tubular portion which has higher radial stiffness) will ideally be substantially equal to the nominal diameter of the body vessel. This will allow for maximal crush resistance. A HRF portion which is sized larger than the nominal diameter may produce extra stress on the vessel wall. A HRF portion which is sized smaller than the nominal diameter may lead to caging and/or thrombosis. However, although ideally the diameter of the HRF zone will be substantially equal to the nominal diameter, it may be somewhat smaller than the nominal diameter. For instance, it may be suitable to place a device having HRF body diameter of 11.5 mm into a vessel with a nominal diameter of about 12 mm.

The LRF zone (or tubular portion which has lower radial stiffness), on the other hand, continually exerts a force on the wall of the vessel, albeit with a lower magnitude. The LRF zone, with its lower radial stiffness, is sized to be somewhat larger than the nominal diameter of the portion of the vessel into which it is implanted. This zone can be of a number of different constructions. In the embodiment of FIG. 2, it has a similar ring structure as the HRF zone in order to increase ease of manufacture, but any design which allows for anchoring the device and maintaining vascular patency can be employed.

In another embodiment, the difference in radial force profile between one zone and another of the device may be generated by constructing each zone of a different material, such as shape memory metals with differing nickel:titanium ratios. In another embodiment, heat-setting of the various portions of the device at different temperatures may be used to modify the radial force profile of the device.

The TZ may also be of a variety of designs. In some embodiments, the TZ may be a single ring. In another embodiment, the TZ may consist of two rings connected together. In another embodiment, the TZ may be more than two rings. In a further embodiment, the TZ may simply comprise a T-bar connecting the HRF body to the LRF body.

The device may further incorporate radiopaque markers to assist a physician with placement in the body. Many suitable radiopaque materials are known and any of these may be selected for use with a device of the present disclosure. The radiopaque markers may be housed in eyelets 62 at the ends of the device, or eyelets 64 which are placed in the transition zones in order to guide the physician to accurately place the HRF zone of the device within the portion of vein affected by the lesion. The radiopaque markers may be made of materials including gold, palladium, tantalum, platinum, and biocompatible alloys of any of these materials.

The device may be of unitary construction. In one sense, a device of unitary construction is made of a single piece of precursor material. One particular example of a device of unitary construction is one that is cut from a cannula. Specifically, a cannula of a shape-memory metal such as a nickel-titanium alloy may be laser-cut to yield the device.

In another embodiment, the device may be made of several separately-formed tubular bodies and attached to one another end-to-end. The attachment may be achieved by welding, for example, or by any other conventional means known in the art.

Figure 4:
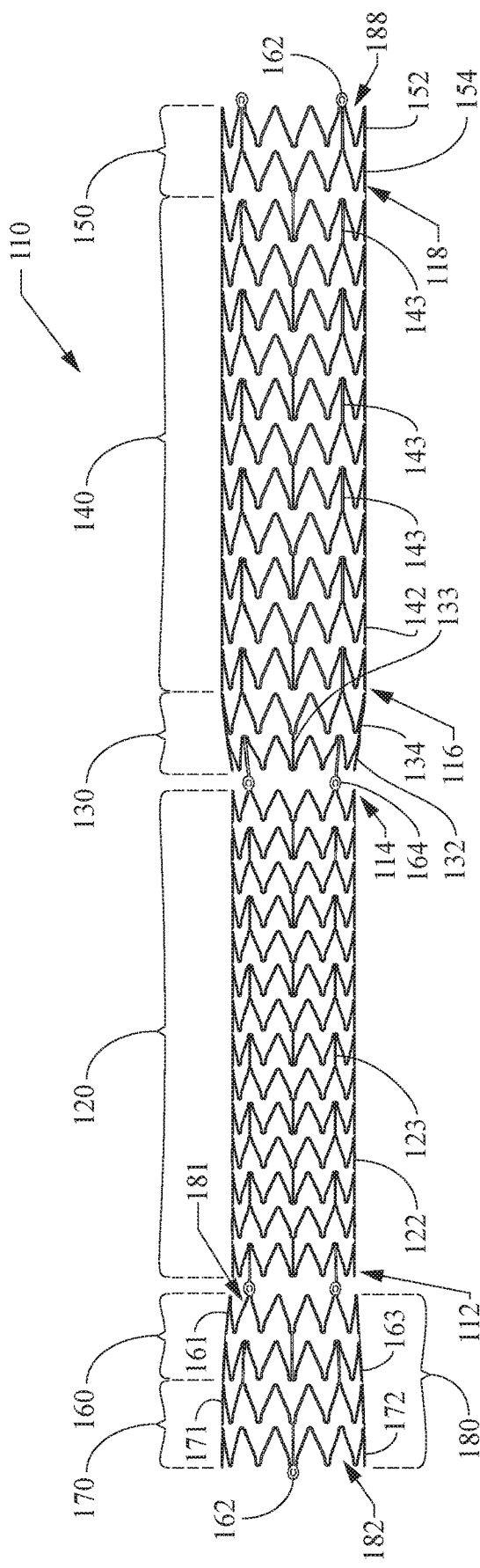
FIG. 4 is a side view of a second embodiment of a device in accordance with the principles of the present disclosure.

FIG. 4 shows a second embodiment of a device having multiple diameters and multiple radial force regions. In this case, the device includes multiple LRF regions. The first tubular portion 170, extending from first end 182 to second end 171, is an end cell pair, which is the first LRF body of the device 110. First transition zone (or transition portion) 160 lies between the second end and the third end 112 of second tubular portion 120 and comprises rings 161 and 163. The second tubular portion 120 extends from third end 112 to to fourth end 114. Second transition zone (or transition portion) 130 is attached to fourth end 120 and third tubular portion 140, which is another LRF body. Third tubular portion 140 extends from fifth end 116 to sixth end 118, and an end cell pair 150 is attached at sixth end 118. Radiopaque markers 162 are positioned at the extreme ends of the overall device and internal radiopaque markers 164 are present in the transition zones. The HRF second tubular portion 120 has a smaller diameter and cross section than any portion of either of the two LRF bodies 170/140. In some embodiments, the two LRF bodies may have the same diameters as one another. In some embodiments, the diameters of the LRF bodies are different. In some embodiments, the LRF bodies are simply end cell pairs, which make up an entire LRF body. The first transition portion 160 has a tapering profile such that its diameter, at any point along its length, is equal to the diameter of the first tubular portion 170, the second tubular portion 120, or is between the diameters of these two portions. The radial stiffness of the first transition portion 160, at any point along its length, is equal to the first radial stiffness of first tubular portion 170, second tubular portion 120, or is between these two values. In a similar way, the diameter and radial stiffness of the second transition portion 130 is equal to the values of these parameters of the second tubular portion 120 and the third tubular portion 140, or between these values.

The addition of two LRF zones at opposite ends of the HRF body allows for multiple points of contact between the device 110 and the walls of the vessel to which it is to be deployed. As such the entire lesion or area subjected to external compression may be bridged, with the smaller-diameter HRF body exerting substantially zero net chronic radial force at the affected portion of the vessel and being anchored by the larger-diameter LRF bodies on either end. Such a device might have superior retention at the site to be treated.

In one embodiment, the device of FIG. 4 has certain specific dimensions. For instance, if the device is to be deployed in a common iliac vein, the diameter of the HRF zone may be about 12 millimeters (mm) and the diameter of the LRF bodies may be about 14 mm. The length of the entire device, therefore, may be about 147 mm, or between about 140 mm and about 150 mm. The width of a strut or segment of the intraluminal support device may be about 0.165 mm. The rings of the HRF body 120 may have a cell length of about 3.6 mm, and the ring structures of the LRF zone 140 may have a cell length of about 4.6 mm. The end cell pair, which comprises two rings, may have a cell length for ring 154 of about 1.8 mm and a cell length for ring 152 of about 5 mm. The transition zones 130 and 160, which in one embodiment comprise two rings, may have a cell length of about 3.9 mm for ring 132/161 and about 4.2 mm for ring 134/163. Ring 171 of LRF body 170 may have a cell length of about 4.8 mm, and ring 172 may have a cell length of about 5.0 mm. The overall length of bodies 170 and 160 (taken together as region 180) may be about 18.26 mm. The overall length of HRF body 120 may be about 51.96 mm. The overall length of transition zone 130 combined with LRF body 140 and end cell pair 150 may be about 70.18 mm. Such a device may have a loading diameter in the compressed state of about 6 to about 8 French. However, it will be appreciated that many different designs are possible for treating a wide variety of lesions or compression-related conditions in a wide variety of vessel sizes.

Much as the device of FIG. 4 incorporates multiple LRF regions, this disclosure also contemplates the employment of devices having multiple HRF regions in cases where multiple compressive lesions might occur. Such devices might be constructed with transition zones between each HRF and LRF.

Figure 5:
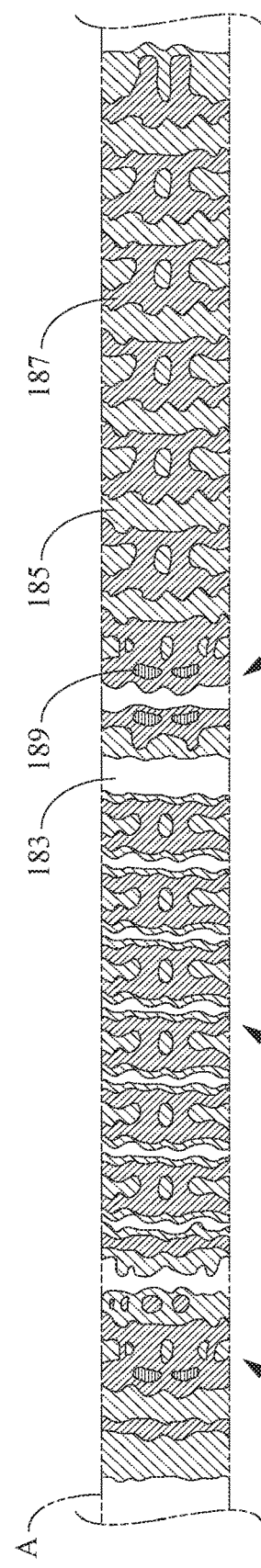
FIG. 5 is a heat map of radial force generated by the device illustrated above it in FIG. 4.

A heat map illustrating the radial force characteristics of the device of FIG. 4 is illustrated in FIG. 5. FIG. 5 is drawn such that it substantially lines up with the illustration of FIG. 4. For the purposes of this illustration, the device 110 has been deployed into a vessel A which has a diameter of about 12 mm.

In FIG. 5, portions 183 (white coloration) exert the lowest radial force on the vessel A into which they are deployed; these regions are substantially in line with the gaps between the transition zones 130/160 and the HRF body 120 where the only structures present are T-bars or connecting members bearing eyelets 164 to contain radiopaque markers for positioning. A great number of white bands 183 are seen within the HRF region. The vessel walls A experience a substantially lower chronic radial force at the point of deployment of HRF body 120 because the diameter is properly sized to the vessel diameter, i.e. its 12 mm diameter is substantially the same as the diameter of the body 120.

A slightly higher force, though still quite low, is generated at portions 185 (wide cross hatching). This is generally seen at the inter-ring spaces of the LRF zones and at the vertices of the HRF rings. Thus the larger diameter of the LRF zones drives increased contact and anchoring of the device while the HRF zone only weakly contacts the wall and provides resistance only when external pressure is applied. The end cell pairs 150/170 also generate about this amount of force.

The next highest regions of radial force are portions 187 (narrow cross hatching). These generally occur wherever the majority of the lengths of the struts of a ring structure contact the wall. The zones of force amount 187 are larger in the LRF body 140 than in the HRF body 120.

The portions of the vessel A which experience the highest level of chronic radial force in FIG. 5 are labeled 189 (horizontal shading). These areas occur exclusively in this embodiment at the transition zones 160 and 130. It is thought that the smaller cell length of the rings that constitute the transition zones, combined with the fact that their diameters are slightly larger than the diameter of the vessel.

The devices of FIGS. 2 and 4 are of an open-cell construction. As is known in the art, devices with closed cell structures can suffer from foreshortening, which increases unpredictability when deploying the device and can lead to difficult implantation. Moreover, closed cell structures have greater length when compressed and loaded into delivery systems, which reduces options for delivery.

An intraluminal support device as described herein may be, in one embodiment, of unitary construction. For instance, the device may be laser cut from a single tube. One choice of material for the tube is a nickel-titanium shape-memory metal. Unitary construction and laser cutting allows for the use of a single pattern to generate the device without the complications and possibilities for introduction of error that derive from weaving, soldering, or using another method to connect separate parts into a unit. As used herein, the term "unitary" means that the device is made of a single piece which has not been joined to another piece.

Further, a device as disclosed herein may be used with many existing delivery systems as are known in the art. Particularly when a device is made of a shape memory metal such as a nickel-titanium alloy, the final dimensions of the device are determined by the remembered state and not dependent upon manipulating the delivery system to crimp or otherwise modify the device as it is being loaded.

Many possible variations on a device of this construction are also possible. If desired, the intraluminal support device may be covered with a water-permeable or an impermeable coating. The support device may be covered with a porous or non-porous layer which has drug-eluting properties. For long-term treatment where ingrowth of the device into the vasculature is desired, a biologically-derived matrix such as an extracellular matrix, a dura mater composition, or any other growth-supporting material may be incorporated. To further support the anchoring of the LRF regions to the vessel, hooks or barbs may be incorporated onto the outer surface of the device. These may be cut from the structure and bent outward or they may be formed of separate pieces and attached by, for example, soldering. All coatings or biological coverings may be attached by any known method, including spray coating, weaving, suturing, and the like.

Figure 6:
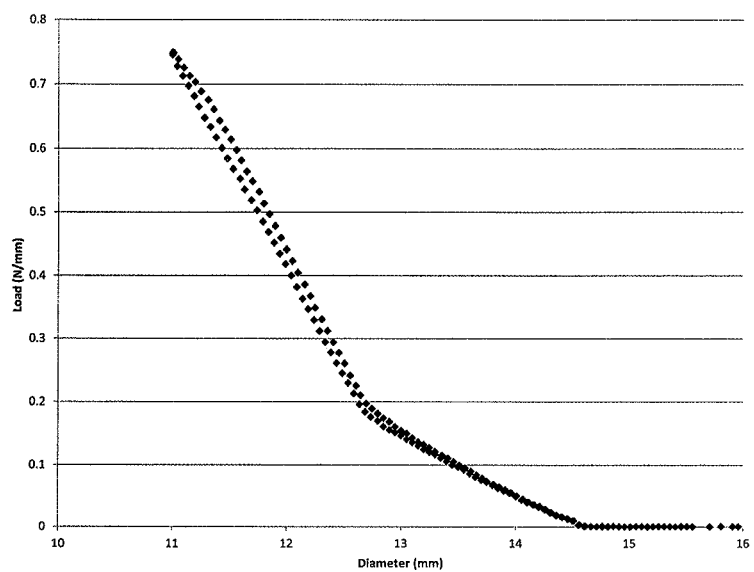
FIG. 6 is a graphical representation of the radial force characteristics of a device constructed in accordance with an embodiment of the present disclosure.

The radial force profile of a device as illustrated in FIG. 4 is shown in FIG. 6. To generate this graph, an intraluminal support device is placed into a testing machinery which applies a constant radial force along the length of the entire device. A radial force is observed when the device is compressed to about 14.5 mm, and increases linearly as the diameter decreases and as the LRF bodies are compressed. When the diameter is compressed to about 12.5 mm, the HRF body (which was too small in diameter to be affected prior to this point) experiences a compressive force, and the slope sharply increases as the entire device including the HRF section experience compression. This too trends linearly to the final diameter of about 11 mm. Therefore it can be seen that the HRF body truly has a higher radial stiffness than the LRF bodies.

Figure 7:
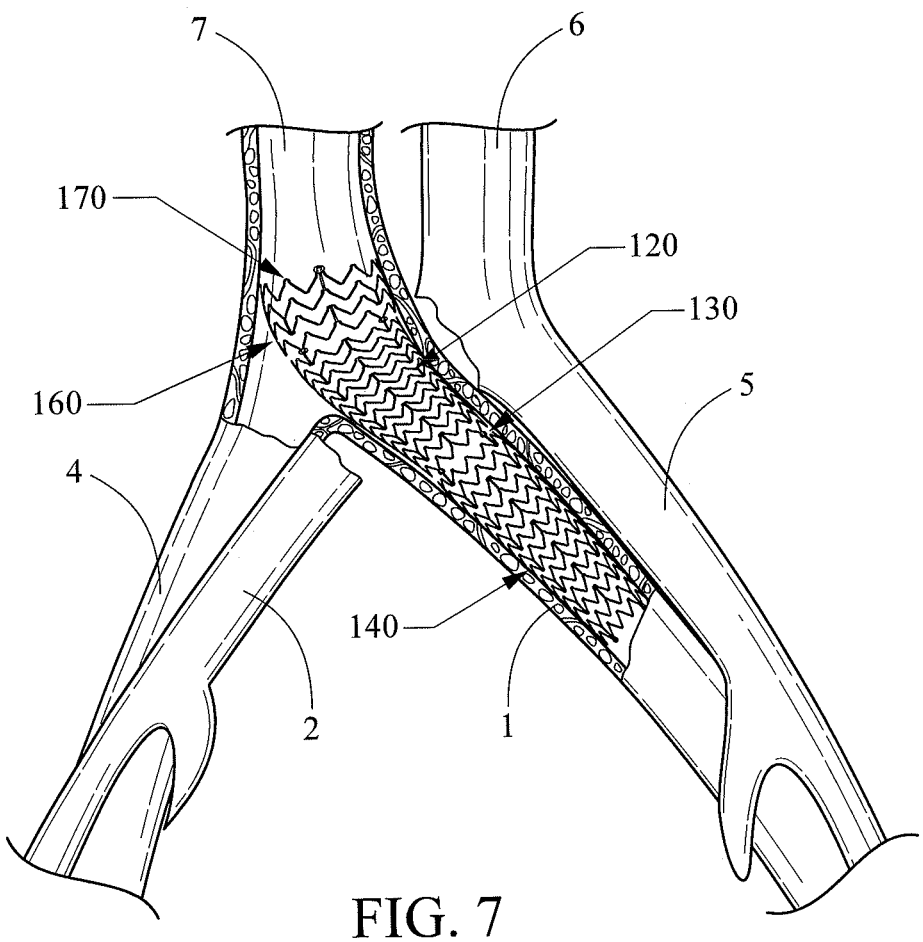
FIG. 7 is a view of an intraluminal support device implanted in an iliac vein in accordance with an embodiment of the present disclosure.

FIG. 7 is a view of a device as illustrated in FIG. 4 implanted in the left common iliac vein 1. The HRF body 120 lies at the point where the right common iliac artery 2 creates a compressive area 3 and reduces the effective diameter of the vein 1. Installation of the HRF zone at this point resists the crushing force generated by the artery. Meanwhile, the LRF zones 140 and 170 anchor the device within the iliac vein and the inferior vena cava 7, respectively, with the larger diameter regions expanding to their remembered states to make consistent contact with portions of the vessels which are not affected by compression. The transition zones 130/160 allow for less-abrupt changes in radial force profile between the LRF portions and the HRF body. It should be noted that the deployed intraluminal support device depicted in FIG. 7 may be deployed in other ways, and that FIG. 7 only represents a single position at which the device may be implanted. For instance, the device may be deployed such that the LRF zone 170 may not make contact with the wall of the inferior vena cava 7; in such a case, the end cell pair would simply stand freely in a vessel lumen without contacting a vessel wall. The device could also be modified, for instance, to have a fenestration in LRF zone 170 or transition zone 160 at a point where the inferior vena cava 7 branches into right common iliac vein 4. Furthermore, the device could be used in conjunction with other implants in a double-barrel stenting operation in order to avoid a portion of the device being set against the wall of the inferior vena cava.

A device in accordance with the principles of the present invention may be useful in treating an acute compressive lesion, such as one caused by a compressive tumor, or by May-Thurner Syndrome. However, a device of this construction may also be useful in treating a diffuse disease in which chronic outward radial force is to be minimized. One such condition is post-thrombotic syndrome (PTS). Patients with PTS have generally experienced a DVT and suffer from less-functional vessels. There may be obstruction from clots, venous insufficiency, rupture of small superficial veins, subcutaneous hemorrhage, and tissue permeability. Because the veins may be weakened or compromised, minimizing chronic outward radial force in stenting treatment of PTS may assist in avoiding complications from the condition.

A device in accordance with the principles of the present disclosure may be made according to a series of steps. As mentioned previously, a single, monolithic, unitary tube of a shape memory alloy may be precisely laser cut to generate the overall shape of the cells of the device. However, such a tube will be restricted to having a single diameter. Thus, one way of making such a device might involve multiple, iterative heat-setting steps, wherein the device may be heat set over a series of mandrels having slightly different dimensions.

In one example, the laser-cut intraluminal support device may be generated from the precursor tube at substantially the diameter of the smaller diameter HRF body. Then, the LRF portions, which are to have a larger diameter in the finished product, may be placed over slightly larger mandrels, heat set, returned to their base temperatures, and then may have this step repeated as many times as is necessary to ensure that the proper diameters of end are reached. In one embodiment, the diameter of a first LRF body may be the same as of a second LRF body. In another embodiment, the diameter of a first LRF body may be smaller than of the second LRF body.

In another example, the precursor tube may be of the final, larger diameter of the LRF regions. In such a case the iterative heat setting steps may involve crimping the central HRF body around successively smaller mandrels until the desired diameter is reached.

In some cases, the transition zones may be specifically heat set over specialized frustoconical mandrels. In other embodiments, the transition zones may form their profiles naturally as the smaller and larger diameter regions are defined by iterative heat-setting steps.

A method of using a device as described in the instant disclosure can include a number of different steps. In one step, the intraluminal support device may be compressed to a compressed state and loaded into a delivery assembly. The delivery assembly may be introduced to the body, possibly percutaneously, and the device delivered, such as by a pusher, into the body lumen in need of treatment. The device, upon deployment, will anchor against the lumen (or vessel) wall at its larger diameter, low radial force bodies, and will bridge the area of potential compression with a high radial force portion having a smaller diameter. Delivery may be guided by imaging which may optionally include monitoring of one or more radiopaque portions included on the device. Finally, the delivery assembly is removed from the patient.

Although an intraluminal support device having variable radial force profiles and varying diameters has been described largely as being of particular use in the circulatory system, the principles of such a device can be broadly employed throughout the body. People or animals experiencing a crushing wound to the esophagus, for instance, may benefit from an implant which is anchored around the injury by low radial force-producing bodies and the wounded area bridged by a high radial-force producing, smaller diameter segment which is sized such that it will have substantially zero net chronic radial force under ordinary conditions but will resist further crushing if an external pressure is applied. Similar uses may also be found in the body lumens of the endocrine and digestive systems While the present invention has been described in terms of certain preferred embodiments, it will be understood that the invention is not limited to the disclosed embodiments, as those having skill in the art may make various modifications without departing from the scope of the following claims.

The invention claimed is:

1. A radially expandable intraluminal support device for implantation into a lumen of a body vessel having a nominal diameter, the device comprising:
   a first tubular portion having a first end extending to a second end and defining a longitudinal axis therethrough, the first tubular portion comprising at least one ring structure and having a first diameter along a first length of the first tubular portion, the first diameter being greater than the nominal diameter in a fully expanded state, the ring structure of the first tubular portion having a first longitudinal cell length, the first tubular portion having a first radial stiffness;
   a second tubular portion having a third end and extending about the longitudinal axis to a fourth end, the second tubular portion comprising at least one ring structure and having a second diameter along a second length of the second tubular portion, the second diameter in the fully expanded state being substantially equal to the nominal diameter, the ring structure of the second tubular portion having a second longitudinal cell length less than the first longitudinal cell length, the second tubular portion comprising a plurality of second rings disposed coaxial with each other, each second ring individually comprising a plurality of second segments arranged as a plurality of peaks and valleys, adjacent second rings are connected to one another by at least one longitudinal connecting segment, the second tubular portion having a second radial stiffness greater than the first radial stiffness; and
   a transition portion between the first tubular portion and the second tubular portion, the transition portion having a length and comprising at least one ring structure and being connected to the second end and the third end, the transition portion having a tapering profile such that the diameter of the transition portion, at any point along its length, has a diameter which is between the first diameter and the second diameter inclusive, the transition portion having a radial stiffness which increases progressively along its length, the radial stiffness of the transition portion increasing from the first radial stiffness at a position at or near the second end to the second radial stiffness at a position at or near the third end;
   where radial stiffness of the first and second tubular portions is the ability of the first and second tubular portions to resist a compressive force applied perpendicular to an outer surface of the first and second tubular portions.

2. The intraluminal support device according to claim 1 wherein, when the device is implanted into the lumen of the body vessel, the second tubular portion produces a greater average outward radial force than the first tubular portion when the body vessel is subject to an external compressive force.

3. The intraluminal support device according to claim 1 wherein, when the device is implanted into the lumen of the body vessel, the first tubular portion produces a greater average outward radial force than the second tubular portion when the body vessel is not subject to an external compressive force.

4. The intraluminal support device of claim 1 further comprising:
   a third tubular portion having a fifth end and extending to a sixth end about the longitudinal axis, the third tubular portion comprising at least one ring structure disposed as in the first tubular portion, the third tubular portion having a third diameter greater than the second diameter in the fully expanded state, the third tubular portion having a third radial stiffness less than the second radial stiffness; and
   a second transition portion comprising at least one ring structure between the second tubular portion and the third tubular portion, the second transition portion having a length and being connected to the fourth end and the fifth end, the second transition portion having a tapering profile such that the diameter of the transition portion, at any point along its length, has a diameter which is between the third diameter and the second diameter inclusive, the second transition portion having a radial stiffness which increases progressively along its length, the radial stiffness of the second transition portion increasing from the third radial stiffness at a position at or near the fifth end to the second radial stiffness at a position at or near the fourth end.

5. The intraluminal support device of claim 1 wherein the first tubular portion comprises a plurality of first rings disposed coaxial with each other, each first ring individually comprising a plurality of first segments arranged as a plurality of peaks and valleys, each first segment having a first length, each ring having its respective peaks aligned with the peaks of all other rings to define an in-phase relationship of the rings along the first tubular portion.

6. The intraluminal support device of claim 5 wherein a peak of one first ring is connected to a peak of an adjacent first ring by a peak-connecting segment.

7. The intraluminal support device of claim 5 wherein a valley of one first ring is connected to a valley of an adjacent first ring by a valley-connecting segment.

8. The intraluminal support device of claim 5 wherein each second segment has a second length less than the first length, each ring having its respective peaks aligned with the peaks of all other rings to define an in-phase relationship of the rings along the second tubular portion.

9. The intraluminal support device of claim 8 wherein a peak of one second ring is connected to a peak of an adjacent second ring by a peak-connecting segment.

10. The intraluminal support device of claim 1 wherein the diameter of the transition portion decreases substantially linearly from the first tubular portion to the second tubular portion.

11. The intraluminal support device of claim 1 wherein the transition portion comprises a plurality of transition rings, the diameter of the transition ring adjacent the first tubular portion having a diameter smaller than the diameter of the first tubular portion, the transition ring adjacent the second tubular portion having a diameter larger than the diameter of the second tubular portion and smaller than the diameter of the transition ring adjacent the first tubular portion, each transition ring between the first tubular portion and the second tubular portion increasing in diameter as its distance from the second tubular portion increases.

12. The intraluminal support device of claim 1 further comprising an end ring attached to the first end and coaxial with the first tubular portion, the end ring having a larger diameter than the first tubular portion and a radial stiffness less than the first radial stiffness.

13. The intraluminal support device of claim 1 wherein the intraluminal support device is of unitary construction.

14. The intraluminal support device of claim 13 wherein the intraluminal support device is formed from a single cannula of shape-memory metal.

15. The intraluminal support device of claim 1 further comprising at least one radiopaque element located between the transition portion and the second tubular portion.

16. A radially expandable intraluminal support device for implantation into a lumen of a body vessel having a nominal diameter, the device comprising:

a first tubular portion having a first end extending to a second end and defining a longitudinal axis therethrough, the first tubular portion comprising at least one ring structure and having a first diameter along a first length of the first tubular portion, the first diameter being greater than the nominal diameter in a fully expanded state, the ring structure of the first tubular portion having a first longitudinal cell length, the first tubular portion having a first radial stiffness;

a second tubular portion having a third end and extending about the longitudinal axis to a fourth end, the second tubular portion comprising at least one ring structure and having a second diameter along a second length of the second tubular portion, the second diameter in the fully expanded state being substantially equal to the nominal diameter, the ring structure of the second tubular portion having a second longitudinal cell length less than the first longitudinal cell length, the second tubular portion comprising a plurality of second rings disposed coaxial with each other, each second ring individually comprising a plurality of second segments arranged as a plurality of peaks and valleys, adjacent second rings are connected to one another by at least one longitudinal connecting segment, the second tubular portion having a second radial stiffness greater than the first radial stiffness; and a transition portion between the first tubular portion and the second tubular portion, the transition portion having a length and comprising at least one ring structure and being connected to the second end and the third end, the transition portion having a tapering profile such that the diameter of the transition portion, at any point along its length, has a diameter which is between the first diameter and the second diameter inclusive, the transition portion having a radial stiffness which increases progressively along its length, the radial stiffness of the transition portion increasing from the first radial stiffness at a position at or near the second end to the second radial stiffness at a position at or near the third end;

wherein the intraluminal support device is of unitary construction, and radial stiffness of the first and second tubular portions is the ability of the first and second tubular portions to resist a compressive force applied perpendicular to an outer surface of the first and second tubular portions.

* * * * *